United States Patent [19]

Hanschen et al.

[11] Patent Number: 5,424,025
[45] Date of Patent: Jun. 13, 1995

[54] PROCESS OF MAKING ZONE ORIENTATED CONTINUOUS WEB

[75] Inventors: Thomas P. Hanschen, St. Paul, Minn.; Dennis L. Krueger, Hudson Township, St. Croix County, Wis.; Stanley C. Erickson, Stillwater; Robert J. Kinney, Woddbury, both of Minn.

[73] Assignee: Minnesota Mining and Manufacturing Company, St. Paul, Minn.

[21] Appl. No.: 56,185

[22] Filed: May 3, 1993

[51] Int. Cl.⁶ .............................. B29C 55/06
[52] U.S. Cl. .................... 264/288.8; 264/289.3
[58] Field of Search ........... 264/280, 288.4, 288.8, 264/289.3

[56] References Cited

U.S. PATENT DOCUMENTS

| 3,783,871 | 1/1974 | Sabee | 128/287 |
| 3,867,940 | 2/1975 | Mesek et al. | 604/366 |
| 4,153,664 | 5/1979 | Sabee | 264/280 |
| 4,210,144 | 7/1980 | Sarge, III et al. | 604/365 |
| 4,296,750 | 10/1981 | Woon et al. | 604/390 |
| 4,539,256 | 9/1985 | Shipman | 428/315.5 |
| 4,623,323 | 11/1986 | Herrington | 493/338 |
| 4,643,730 | 2/1987 | Chen et al. | 604/390 |
| 4,650,451 | 3/1987 | Herrington | 264/288.8 X |
| 4,654,021 | 3/1987 | Herrington | 493/211 |
| 4,654,180 | 3/1987 | Herrington | 264/288.8 |
| 4,684,359 | 8/1987 | Herrington | 264/288.8 X |
| 4,902,553 | 2/1990 | Hwang et al. | 428/156 |

OTHER PUBLICATIONS

Abstract of Japan 56-109,716 (published Aug. 31, 1981).

Primary Examiner—Leo B. Tentoni
Attorney, Agent, or Firm—Gary L. Griswold; Walter N. Kirn; William J. Bond

[57] ABSTRACT

A continuous web with longitudinaly displaced thick and thin zones. The thin zones being uniaxially orientated. The web is useful in forming diaper backsheet films where the thick zones act as a reinforced zone for attachment of a pressure-sensitive fastening tab.

5 Claims, 5 Drawing Sheets

PROCESS OF MAKING ZONE ORIENTATED CONTINUOUS WEB

FIELD OF THE INVENTION

The present invention relates to a method for providing a reinforced zone on a substrate web particularly a diaper backsheet film. More particularly, the invention relates to an orientatable thermoplastic web material having selective high strength attachment zones for use in a refastenable pressure-sensitive adhesive fastening tab diaper closure system.

BACKGROUND OF THE INVENTION

Disposable diapers and similar articles are commonly provided with closure systems. The closure comprises two opposing elements to be joined and fastener elements to effect this joining or closure. In conventional systems, the fastening elements are pressure-sensitive adhesive(PSA) fastening tabs permanently adhered to one element at one end(the manufacturers end) and preferably refastenably adhered to a second opposing element at a second end(the free end) of the fastening tab. With a disposable diaper, the two opposing elements or attachment surfaces are sides of the diaper and the PSA fastening tab is conventionally adhered at both ends to the same thin outer water-impermeable backsheet material, which conventionally is a thin polyethylene film (e.g., less than 1 mil thick). Therefore, the diaper PSA fastening tab has the conflicting goals of permanently and refastenably adhering to the same thin polyethylene film at opposing ends of the same tab. This is problematic as the same adhesive is used on both ends of the fastening tab, and a pressure-sensitive adhesive designed to permanently attach a tab to a thin diaper backsheet film will conventionally tear these thin films when the tab is removed, while adhesives designed to refastenably adhere a tab to a thin diaper backsheet film has a tendency to adhesively fail. A common solution proposed for this problem has been to strengthen the thin backsheet film with a reinforcement material in the diaper frontal region, at least where the free end of the tab is to be refastenably adhered, to prevent tearing. A common commercial approach has been to adhere a pressure-sensitive adhesive tape to the outside of the diaper backsheet film at this frontal region where the tab free end is refastenably attached. The tape backing acts as a reinforcing material, as well as serving as a predictable attachment surface for the free end of the PSA fastening tab. Alternatively, it has been proposed to place the reinforcement film on the interior surface of the backsheet in the frontal region and/or attach a reinforcement film by use of a hot-melt adhesive.

U.S. Pat. No. 4,643,730, proposes coating the interior of a diaper backsheet film in the frontal region with a radiation-curable coating such as urethane acrylate acrylic oligomers admixed with acrylate acrylic oligomers, epoxy acrylate acrylic oligomers or combinations thereof. However, the method described in this patent is expensive and requires a complicated and difficult-to-predict curable coating admixture.

U.S. Pat. No. 4,296,750 describes a diaper backsheet film reinforced with a hot-melt adhesive layer selectively applied to the portion of the backsheet refastenably adhered too by the free end of the fastening tab, i.e. the frontal region. Again, this solution is somewhat expensive and the temperature employed in applying the hot-melt adhesive layer generally has a tendency to distort or degrade thin polyethylene films. U.S. Pat. No. 4,210,144 similarly proposed applying hot-melt adhesive in the "mother's bond region" of the diaper backsheet where the adhesive fastening tab free end is releasably adhered(the frontal region). This patent describes applying adhesive glue beads or patterns of adhesive including continuous adhesive coatings. The adhesive beads are applied so that they span the width of the mother's bond region in the direction parallel with the direction of fastening tab attachment and removal. Again, this solution can adversely effect thin diaper backsheet films.

U.S. Pat. No. 3,867,940 proposes adhesively applying a scrim or a film to the mother's bond region, among other regions, of a diaper backsheet. The scrim or polymer film (e.g., biaxially orientated polyethylene terephthalate) can be applied to either the interior or exterior surface of the backsheet. The reinforcement described in this patent is the general commercial practice, however, the art continues to look for alternative methods.

U.S. Pat. No. 3,783,871 proposes reinforcing a diaper in the mother's bond region or refastening area by making the backsheet thicker in the areas where the fastening tab is adhered. The described method for selectively thickening the backsheet is a pulsed extruder. This method would be difficult to control and would require large amounts of resin to form the backsheet.

Despite the numerous proposed solutions outlined above, the art continues to search for new and unique ways for solving the problems of refastenability for a pressure-sensitive adhesive closure system, such as a diaper PSA fastening tab closure system using a reinforced frontal region as one attachment surface. The invention product and process provides a unique and highly advantageous structure and method for providing a reinforced region on a thin orientatable film without the use of costly separately applied reinforcement material(s), which reinforced region has a length and width suitable for use as a refastenable attachment surface of a diaper or like articles.

BRIEF DESCRIPTION OF THE INVENTION

The present invention provides a continuous web such as a diaper or incontinent article backsheet material or web (e.g., film) having at least one first untensilized or unorientated (or less tensilized) zone of a first thickness and at least one second longitudinally tensilized or orientated zone of a second thickness thinner than the first thickness, which continuous web is formed by selectively orientating a continuous thermoplastic orientatable web in the machine direction at a stretch ratio of from about 2:1 to 8:1 in the second zone(s), depending on the polymer, providing a thickness ratio of the first zone(s) to second zone(s) of about 1.2 to 6.0. The unorientated zone of a first thickness serves as the reinforced attachment surface(s) and, generally, has a thickness of at least about 1 mil(25μ), preferably at least about 2 mil(50μ).

The invention web is produced by a selective machine direction stretching method and apparatus, including a means for establishing a continuous web substrate path with means for moving the substrate at a first speed along the substrate path. A substrate reinforcing means at at least one select portion of the substrate path provides the first non-, or less, tensilized, or oriented, zone. At least one selective machine direction orientation or elongation means provides a second substrate tensilized or orientated zone of a second thickness. These two means operate sequentially or simultaneously, or both, and preferably at regular repeated intervals. The thickness of the orientated zone is related to the degree of orientation relative to the untensilized substrate web thickness. A cutting means is then supplied for cutting the continuous zone orientated substrate web into discrete unit lengths or, alternatively, the web can be collected on a collection means and subsequently cut as required.

BRIEF DESCRIPTION OF THE DRAWINGS

The invention will be further described in reference to the accompanying drawings, like reference numerals refer to like parts in the several views, and wherein.

DETAILED DESCRIPTION OF THE PREFERRED EMBODIMENTS

Figure 1:
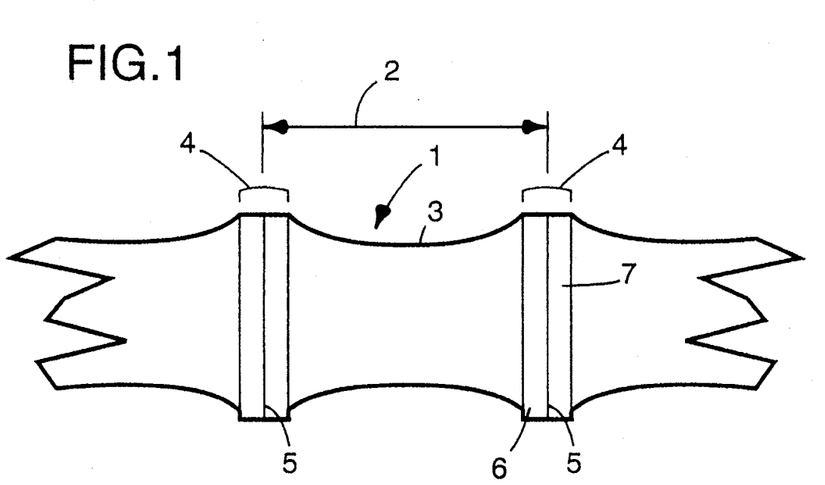
FIG. 1 is a perspective view of a zone orientated film or web material, orientated in discrete zones as would be required for diaper backsheets.

Referring to FIG. 1, a selectively orientated continuous film 1 of a width suitable for forming individual diaper backsheet units is shown with orientated zones 3 and non-orientated zones 4. The thickness of the orientated zones 3 would be dependent on the degree of orientation and the original thickness of the non-orientated film. The thickness of the non-orientated zones 4 is dependent on the thermoplastic polymer forming the film, or web, and the required strength of the film necessary to resist tearing by the selected pressure-sensitive adhesive fastening tab adhered and removed therefrom. Generally, zone 4 will be at least 1 mil (25 microns) and, preferably, about 2 mils(50 microns) or more. The orientated zone 3 will generally be at least 0.3 mils(8 microns), up to about 1.0 mil(25 microns), depending on the draw ratio employed. Zone 3 in FIG. 1 is shown as being necked-in, which is a natural consequence of machine direction orientation without cross direction support. This necked-in region can advantageously form into a shape that corresponds to a leg cutout portion of a diaper backsheet, which normally must be formed by a separate on-line cutting operation. However this neck-in may not be desirable in some instances, for example, were film 1 of a width requiring subsequent slitting into useful widths. The individual diaper backsheet segments 2 can be cut along lines 5 to provide a reinforced frontal section 7, which frontal section 7 has the strength necessary to releasably adhere to a diaper PSA fastening tab or tape (not shown) without tearing, and a reinforced back portion 6, which can be used as a permanent attachment surface for the diaper PSA fastening tab(the manufacturer's end) that is also resistant to tearing. Cut line 5 can be provided at other locations, and/or zones 6 and 7 can be separated by a second smaller oriented zone for attachment of a waist elastic.

The film 1 is formed of an orientatable thermoplastic film with a thickness selected to provide the desired end thickness and resultant tensile properties for the non-orientated zones 4. Appropriate film tensile strengths can be obtained with most film forming polymers including polyolefins; particularly polypropylene, polyethylene, copolymers and blends; polystyrene; polyesters, such as polyethylene terephthalate; polyvinyl chloride; copolymers and blends including blends with elastomeric materials in amounts sufficient to improve toughness, if not render the film slightly elastic. Preferably, the backing film is formed predominately from a polypropylene or polyethylene polymer, copolymer or blend. The film can also include conventional modifiers such as antioxidants, fillers, pigments, or the like. Suitable fillers include titanium dioxide and calcium carbonate, desirable for providing opaque films which, if added in sufficient quantities, can produce a film having interconnected porous structures providing a breathable diaper backsheet. Breathability can also be created by use of film formed from a blend of compatible polymers or a polymer and liquid additive that becomes phase distinct on cooling after extrusion as disclosed in U.S. Pat. Nos. 4,902,553 or 4,539,256. Substrates other than films are also suitable for the invention process including consolidated nonwovens materials, woven materials and laminates.

Figure 2:
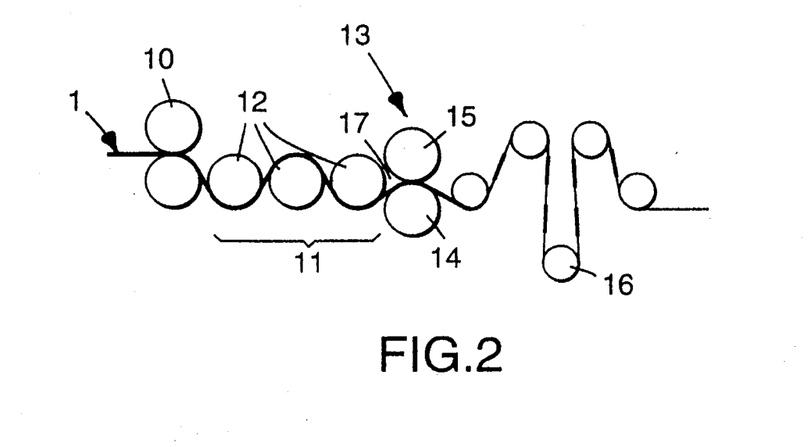
FIGS. 2, 2A, 3, 4A, 4B, 5, 6, 7, 8 and 9 are schematic diagrams illustrating alternative embodiments of the process of the present invention.
Figure 2A:
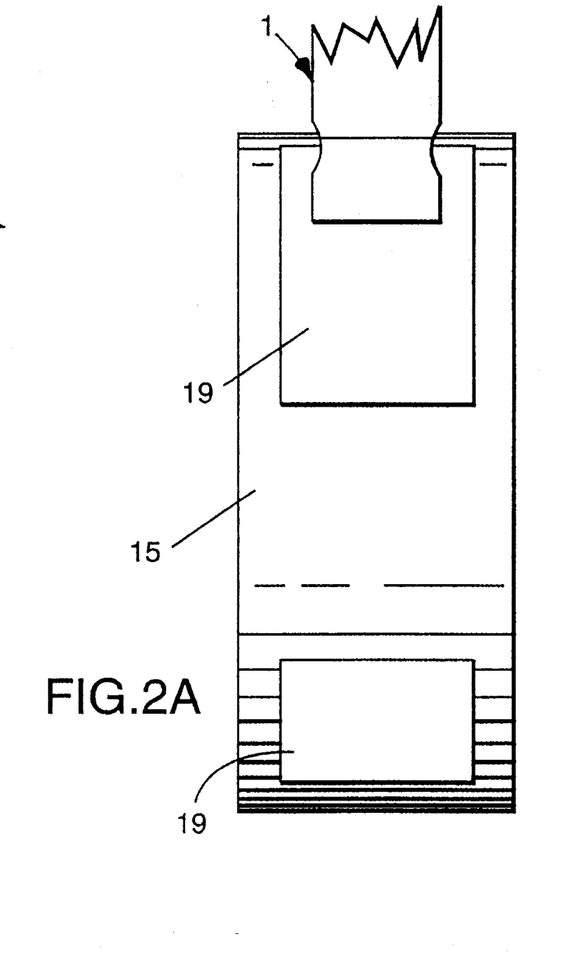

FIGS. 2 and 2A illustrates a first embodiment for preparing the zone orientated film of FIG. 1. The film 1 is provided from a supply means (not shown) into an inlet nip 10 and a heating zone 11, provided by conventional heated rolls 12. Following the heating zone 11, the material can be optionally fed to a secondary inlet nip or fed directly to an orientation nip 13 provided by high speed roll 14 and a patterned rubber roll 15 provided with a series of cutouts 19 as shown in FIG. 2A. When the patterned rubber roll 15 is in contact with roll 14, the cutout regions cause the nip 13 to act as if it were open periodically stopping orientation of the film 1, during these time periods. The non-recessed portions of patterned rubber roll 15, in combination with the high-speed roll 14, close the nip acting as the orientation means. The last roll 12, or the secondary inlet nip, in conjunction with the periodically open nip created by the cutout areas 19 acts as the reinforcement means by periodically allowing film to pass beyond the nip without orientation. The gap 17 between the periodically nipped high-speed roll 14 and the secondary inlet nip or final heated roll 12 is advantageously minimized to reduce any neck-in for a wide film and increased to increase neck-in for a unit width diaper film. Film on exiting nip 13 is preferably fed to a dancer roll 16 maintaining even tension on the downstream side of nip 13 and preventing orientation of the film by downstream driven rolls or take-up devices. The relation of the length of the recessed area(s) in the rubber roll to the high-speed nip roller 14 speed and the gap 17 length is defined by the stretch ratio and the desired unit length for the periodicly orientated continuous film.

Figure 4A:
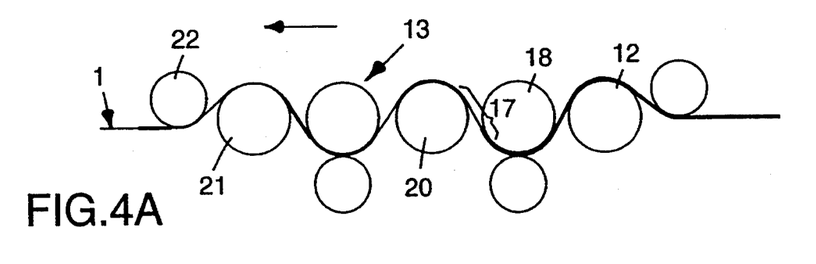
Figure 4B:
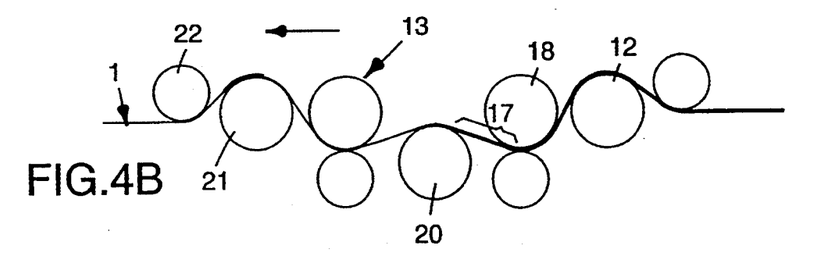

FIGS. 4 A and B display an alternative embodiment for forming the zone orientated film of FIG. 1. FIG. 4 shows an inlet nip 18 following preheating roll(s) 12. High-speed orientating nip 13 is ahead of downstream rolls 21 and 22, which may optionally be cooled to provide an annealing zone. Roll 20 is an oscillating roll driven at the speed of high-speed nip 13. The roll 20 oscillates up and down transverse to the film 1 path of travel. When the oscillating roll 20 is in the up position, the orientation gap 17 of film path between nips 13 and 18 is relatively long resulting in orientation of the film. When the roll 20 is in the down position, the length of the film path and gap 17 decreases, resulting in little or no orientation of film in gap 17 acting as a reinforcement mean and thereby creating region 4. In this embodiment, the roll 20 minimizes the degree of film neckin in region 3. Minimizing neck-in is advantageous when there is a high degree of orientation which can create a neck-in that can reach up to 50 percent of the original cross width of film 1.

Figure 5:
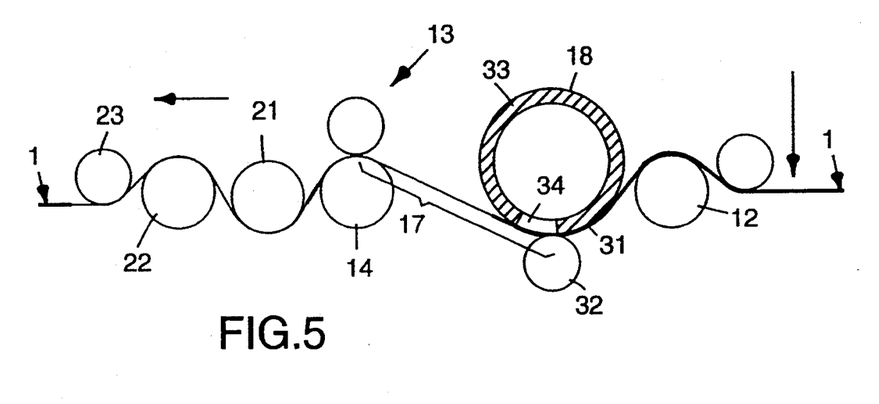

A third alternative embodiment of the invention process is depicted in FIG. 5 where an inlet nip 18 is provided with a roll 31, that is provided with one or more heated zones 33, and one or more cooled zones 34, opposite nip roll 32. The heated zone 33 results in preferential orientation of film softened by the heated zone 33, while cooled zone 34 acts as a reinforcement means for film 1 opposite this zone in nip 18. Outlet high-speed orientation nip 13 creates the orientating tension in gap 17 which gap is greater than or equal to the length of a diaper backsheet unit 2 for the continuous film of FIG. 1. The film will preferentially not undergo orientation in the unheated or cooled region of the film as long as the film is stretched by less than the natural draw ratio in the preferentially orientated heated zones. Preferably, annealing rolls 21 and 22 are provided following the orientation nip 13 to smooth out wrinkles generated during the orientation process.

Figure 3:
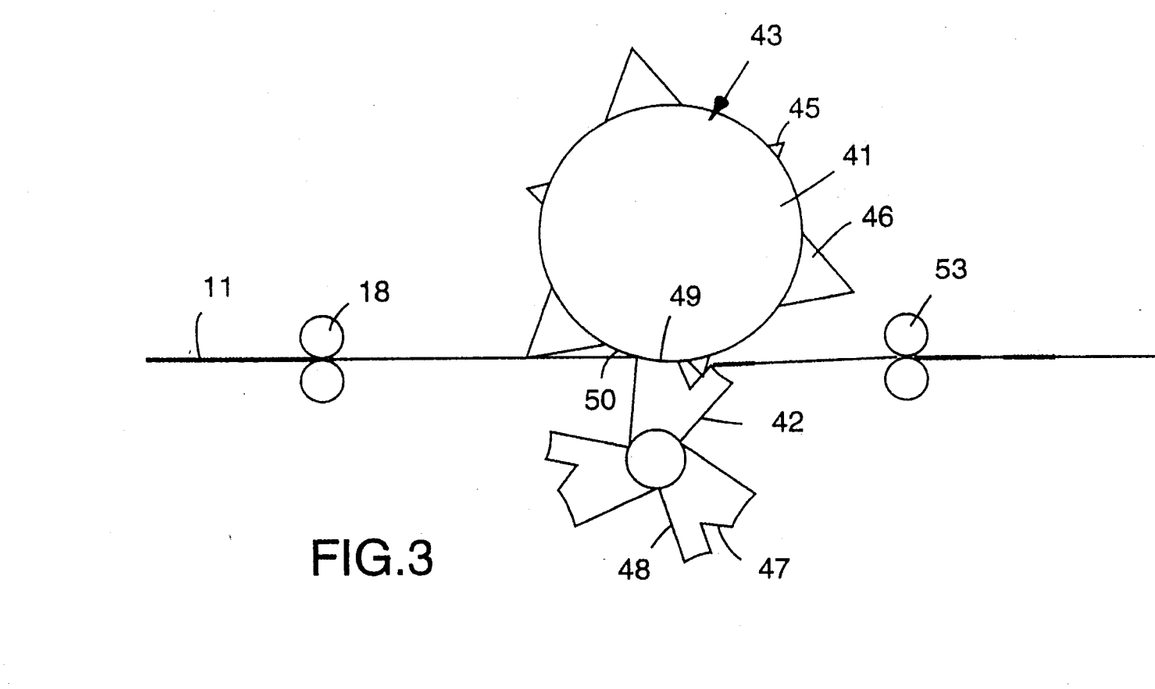

A fourth embodiment of the invention process is depicted in FIG. 3. In this embodiment film 1 is supplied by inlet nip 18 to an orientating roll arrangement 43 comprising interpenetrating male and female rolls 41 and 42, respectively. Projections 45 and 46 of male roll 41 engage the film 1 drafting the film into corresponding depressions 47 and 48 in female roll 42 to preferentially orientate the film 1. The non-orientated regions of the film are provided by reinforcement of the film between land areas 49 and 50 located between the interpenetrating projections and depressions. This method, as in the method described with reference to FIG. 4, minimizes necking of a film material, particularly when the surfaces of the interpenetrating rolls are roughened to prevent or lessen transverse film shrinkage or necking during the orientation step. This process may create a slight amount of transverse or cross direction orientation.

Figure 6:
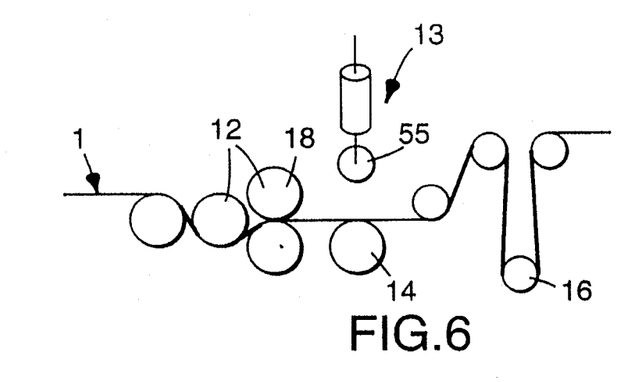

FIG. 6 depicts a fifth embodiment analogous to that described in FIG. 2 where the nip 13 is opened and closed by a pneumatically controlled rubber nip roller 15 rather than cutouts 19 in the roll 15. More than one treatment station can be provided in sequence to provide additional selective orientation.

Figure 7:
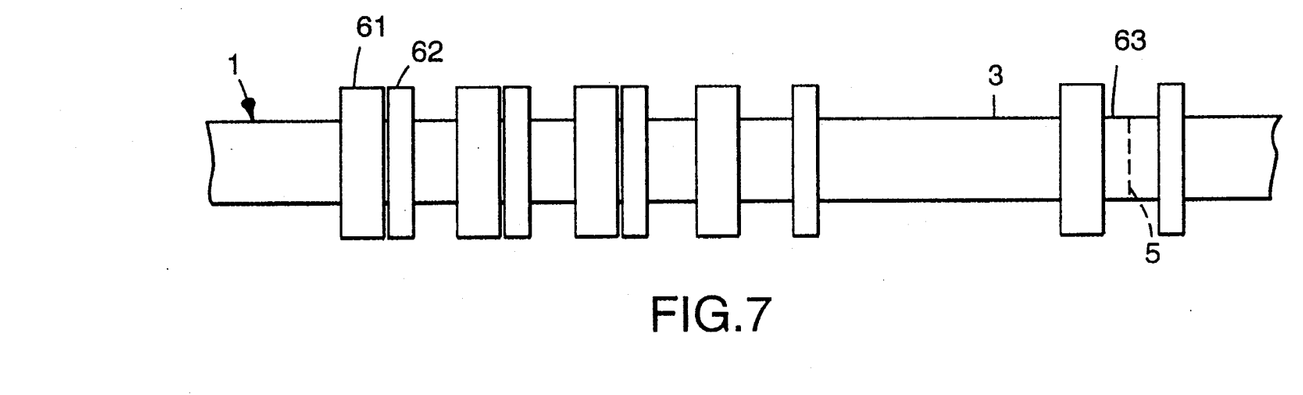

A sixth embodiment of the invention process is depicted in FIG. 7. Reinforcement of the film is accomplished by means of clamps 61 and 62, which engage separate accelerating means, such as a pair of displaced chain drives, variable pitch screws or belt drives (not shown) each provided with means to selectively engage and disengage with clamps 61 and 62. The separately driven clamps 61 and 62 move relative to each other when engaged with the film 1 to provide orientated zones 3 and 63 as shown in FIG. 7. The film is reinforced by the clamps to provide non-oriented regions. The individual diaper backsheet units could then be separated at the indicated cut lines 5 between clamps 61 and 62, as shown, to form separate diaper backsheets.

Figure 8:
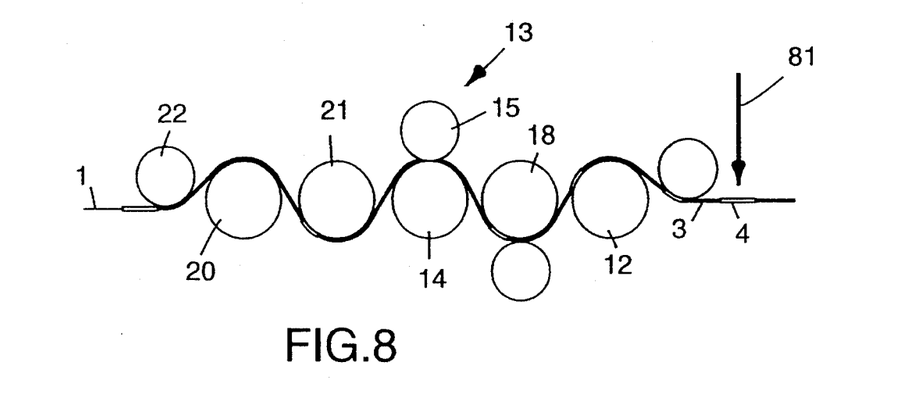

A seventh embodiment of the invention process is depicted in FIG. 8 where reinforcement of the non-orientated regions or zones 4 is provided by crosslinking or crystallizing 81 selected regions 4 of film 1 prior to orientation. This can be accomplished through selective irradiation or a crosslinking heat treatment, optionally with crosslinking agents incorporated into the film 1. The strengthened or reinforced film region 4 allows regions 3 to undergo preferential elongation or orientation between inlet nip 18 and orientation nip 13.

Figure 9:
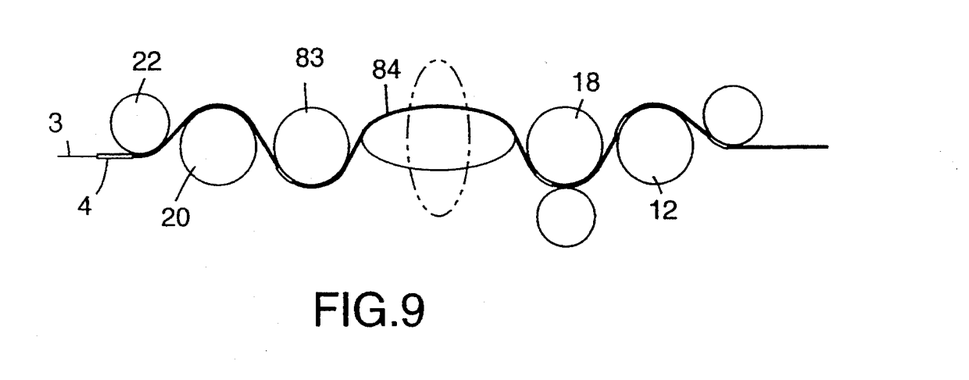

An eighth embodiment of the invention process is depicted in FIG. 9 where the selective film orientation is provided by an elliptical roll 84, between inlet nip 18 and high-speed nip 83. Elliptical roll 84 will alternately lengthening and shortening the film path and orientation gap 17 between the two nips creating periodic elongation or orientation by a process analogous to that described for the FIG. 4A&B embodiment.

An alternative to employing a preheating roll 12 in the above embodiments would be to selectively length orientate a film in selected regions immediately following hot-melt extrusion of the film where the film is allowed to cool to an appropriate temperature prior to the selective elongation process. However preheating rolls can be used following melt extrusion. The alternative processes described above can be used separately or in combination where advantageous. Further, use of optional steps or equipment described with respect to one embodiment can advantageously be used with all embodiments as appropriate. The above embodiments were described relative to a continuous film designed to be cut into reinforced diaper backsheet units however the process would be equally applicable to other webs such as films laminated to a nonwoven or webs designed for other uses.

The following examples represent the present preferred embodiments of the invention film and process and should not be considered limiting thereof unless otherwise indicated.

EXAMPLE 1

A polypropylene (Exxon 1024E1) film was fed into a nip 13, substantially as shown in FIG. 6, except the nip was operated manually (The film was cast onto a casting wheel at a temperature of 56° F. (13° C.) operating at 18 feet per minute (5.5 meters per minute)). The cast film was preheated to 220° F. (104° C.) and fed to a nip, which was periodically opened and closed by hand, with a driven roll operating at 66 feet per minute (20 meters per minute) to provide a draw ratio of 3.7:1. The width of the non-orientated zone 4 was 13.75 inches(35 cm), and the orientated zone minimum width was 12.25 inches(31 cm), providing a maximum neck-in of 11%. The thickness of the non-orientated zone 4 was 4.0 mil(100 microns) with the orientated zone 3 having a minimum thickness of 1.3 mil(33 microns).

EXAMPLES 2-9

These examples were produced on a film line such as that shown in FIG. 2, without an inlet nip 10 and with 5 preheating rolls, with the film 1 being fed directly from an extruder and casting wheel. The cast film was subject to preheating (to 220° F.,104° C.) prior to entering the orientation nip 13 provided with a rubber nip roll 15 having a diameter of 10.5 inches. The nip was similar to that of FIG. 2 except the rolls were horizontally disposed rather than vertically disposed. The rubber roll 15 had two cutout regions, each 10 inches in length and separated by a 2 inch non-recessed area and an 11 inch non-recessed area providing the nipping pressure and creating two orientated regions. The processing conditions are set forth in Table 1.

TABLE 1

| Ex. | Polymer | Cast Wheel | | Orienting Nip | | |
|---|---|---|---|---|---|---|
| | | °C. | Speed M/min | M/minSpeed | Draw Ratio | Preheat Temp |
| 2 | Polypropylene[1] | 27 | 8.3 | 33.5 | 4 | 145 |
| 3 | Polypropylene[1] | 27 | 8.3 | 41.1 | 5 | 165 |
| 4 | Polypropylene[1] | 49 | 8.3 | 41.1 | 5 | 195 |
| 5 | Pe/PP copolymer[2] | 49 | 8.3 | 32.9 | 4 | 165 |
| 6 | Pe/PP copolymer[2] | 49 | 8.3 | 41.1 | 5 | 185 |
| 7 | Pe/PP copolymer[2] | 27 | 8.3 | 41.1 | 5 | 185 |
| 8 | Pe/PP copolymer[3] | 27 | 9.5 | 47.5 | 5 | 153 |
| 9 | Pe/PP copolymer[3] | 27 | 9.5 | 38.1 | 4 | |

[1] Exxon TM 4092
[2] Sheel TM 7C50
[3] Eastman TM P5-011

The films resulting from the above conditions are characterized in Table 2.

TABLE 2

| Ex. | Neck-in % | Thickness (Zone) (Mil) | | Length (in) Unoriented | Length (in) Oriented 1 | Length (in) Oriented 2 |
|---|---|---|---|---|---|---|
| | | unoriented | oriented | | | |
| 2 | 12.5 | 2.4 | 1.3 | 2–3 | 0.25–1.01 | 6.5–7.51 |
| 3 | 16 | 2.1 | 1.0 | 2.5–6 | 0–1.0 | 8–9 |
| 4 | 14.9 | 2.2 | 1.0 | 0.5–2.5 | 1–2 | 9–10 |
| 5 | 10.8 | 2.2 | 0.81 | 2.5–32 | 2[2] | 9.5–10[2] |
| 6 | 11.4 | 2.4 | 0.8 | 1–2 | 2–2.51 | 10.5[1] |
| 7 | 13.5 | 2.5 | 1.0 | 2–2.51 | 2.5–3.51 | 11.5–12 |
| 8 | 3.7 | 2.3 | 0.7 | 1–1.5 | 2.5–3 | 12[3] |
| 9 | 6.5 | 2.2 | 0.8 | 1.5–2 | 3.5–4 | 13–13.5 |

1 island formation
2 large islands
3 edge tears

The formation of islands indicated the initial propagation of orientation and was usually noticed in the transition zones between the thicker unoriented zones and the two orientated zones 1 and 2. The neckin was measured between the thick unorientated zone and the width of the second longer orientated zone 2 where the leg cutouts are made in typical diaper backsheets. The first shorter orientated zone 1 would form the upper top end of the diaper where elastic is typically placed. Placement of standard diaper tapes on the thick unoriented zones did not result in tearing of the film when removed. The thinner oriented zones 1 and 2 were relatively soft to the touch.

EXAMPLE 10

This film was zone oriented using the apparatus of examples 2–9 above with a 2.4 mil(61 micron) film of a 90/10 blend of Shell WRD 6-281(polypropylene impact copolymer)/Shell Kraton TM 1107(styrene-isoprene-styrene block copolymer). The casting wheel was 80° F.(27° C.) at 22.9 fpm(7 m/min). The film was preheated to 120° F.(49° C.). The orientation nip ran at 103 fpm(31.4 m/min)providing a draw ratio of 4.5:1. The film passed over chromed roll 14 of the nip prior to entering the nip. An air knife(82 PSI-58000 Kg/m$^2$) was directed between the roll 14 and the film. The zone orientated film had two orientation zones, one 2.7 inches(6.8 cm) long and one 12.5 inches(31.8 cm) long, the two intervening unoriented zones were both about 1.7 inches(4.3 cm) long. There was a small transition region between the oriented zones and the unoriented zones of about 0.1 inches(0.25 cm) or less. The minimum thickness of the film in the oriented zones was about 0.8 mils(20 microns). The film was excellent in appearance with no significant islands or edge tears.

The various modifications and alterations of this invention will be apparent to those skilled in the art without departing from the scope and spirit of this invention, and this invention should not be restricted to that set forth herein for illustrative purposes.

We claim:

1. A method for zone orientating a web in the machine direction comprising the step of providing a web traveling in a machine direction at a first speed, reinforcing the web in a first zone with a reinforcing means across the width of the web transverse to the machine direction providing reinforced zones, orienting the web in the machine direction, transverse to the reinforcement means, at a second speed with an orientation means comprising a periodically engaging nip provided by a nip roll having cutout regions selectively engaged and disengaged with a driven roll to selectively provide orientated zones adjacent to the reinforced zones thereby providing a zone orientated web wherein the orientated zone web thickness is less than the reinforced zone web thickness.

2. A method for zone orientating a web in the machine direction comprising the step of providing a web traveling in a machine direction at a first speed reinforcing the web in a first zone with a reinforcing means across the width of the web transverse to the machine direction providing reinforced zones, orienting the web in the machine direction, transverse to the reinforcement means, at a second speed with an orientation means to selectively provide orientated zones adjacent to the reinforced zones thereby providing a zone orientated web wherein the orientated zone web thickness is less than the reinforced zone web thickness and said reinforcement means comprises a means to selectively cool the web at a reinforcement zone, relative to the remainder of the web which is heat softened prior to orientation by the orientation means comprising an orientating nip.

3. A method for zone orientating a web in the machine direction comprising the step of providing a web traveling in a machine direction at a first speed reinforcing the web in a first zone with a reinforcing means across the width of the web transverse to the machine direction providing reinforced zones, orienting the web in the machine direction, transverse to the reinforcement means, at a second speed with an orientation means to selectively provide orientated zones adjacent to the reinforced zones thereby providing a zone orientated web wherein the orientated zone web thickness is less than the reinforced zone web thickness and said reinforcement means comprises comprises means to provide a selectively crosslinked web zone comprising the reinforcement zone.

4. A method for zone orientating a web in the machine direction comprising the step of providing a web traveling in a machine direction at a first speed reinforcing the web in a first zone with a reinforcing means across the width of the web transverse to the machine direction providing reinforced zones, orienting the web in the machine direction, transverse to the reinforcement means, at a second speed with an orientation means to selectively provide orientated zones adjacent to the reinforced zones thereby providing a zone orientated web wherein the orientated zone web thickness and said reinforcement means is provided by a shortened web path between an orientating nip, comprising the orientating means, and a feed nip, where the shortened web path is provided by an eccentric roll positioned between the orientating nip and the feed nip.

5. A method for zone orientating a web in the machine direction comprising the step of providing a web traveling in a machine direction at a first speed reinforcing the web in a first zone with a reinforcing means across the width of the web transverse to the machine direction providing reinforced zones, orienting the web in the machine direction, transverse to the reinforcement means, at a second speed with an orientation means to selectively provide orientated zones adjacent to the reinforced zones thereby providing a zone orientated web wherein the orientated zone web thickness and said reinforcement means is provided by clamp means and the orientation means is provided by selectively engaging clamp drive means so that adjacent clamp means are driven at different speeds in the web machine direction selectively orienting the web zones therebetween.

* * * * *

UNITED STATES PATENT AND TRADEMARK OFFICE
CERTIFICATE OF CORRECTION

PATENT NO. : 5,424,025

DATED : June 13, 1995

INVENTOR(S) : Thomas P. Hanschen, Dennis L. Krueger, Stanley C. Erickson and Robert J. Kinney It is certified that error appears in the above-indentified patent and that said Letters Patent is hereby corrected as shown below:

Col. 6, line 23, "Or" should read --or--.

Col. 7, Table 1, "$^2$Sheel TM 7C50" should read --$^2$Shell TM 7C50--.

Col. 7, Table 2, under "Thickness (Zone) (Mil) oriented", Row 5, "0.81" should read --0.8$^1$--.

Col. 7, Table 2, under "Length (in) Oriented 2", Row 2, "6.5-7.51" should read --6.5-7.5$^1$--.

Col. 7, Table 2, under "Length (in) Oriented 1", Row 2, "0.25-1.01" should read --0.25-1.0$^1$--.

Col. 7, Table 2, under "Length (in) Unoriented", Row 7, "2-2.51" should read --2-2.5$^1$--.

Col. 7, Table 2, under "Length (in) Unoriented", Row 5, "2.5-32" should read --2.5-3$^2$--.

Col. 7, Table 2, under "Length (in) Oriented 1", Row 6, "2-2.51" should read --2-2.5$^1$--.

UNITED STATES PATENT AND TRADEMARK OFFICE
CERTIFICATE OF CORRECTION

PATENT NO. : 5,424,025
DATED : June 13, 1995
INVENTOR(S) : Thomas P. Hanschen, Dennis L. Krueger, Stanley C. Erickson and Robert J. Kinney It is certified that error appears in the above-indentified patent and that said Letters Patent is hereby corrected as shown below:

Col. 7, Table 2, under "Length (in) Oriented 1", Row 7, "2.5-3.51" should read --2.5-3.5$^1$--.

Col. 7, line 34, "neckin" should read --neck-in--.

Signed and Sealed this

Twenty-eighth Day of May, 1996

Attest:

BRUCE LEHMAN

Attesting Officer     Commissioner of Patents and Trademarks